United States Patent

Choi et al.

Patent Number: 5,851,727
Date of Patent: Dec. 22, 1998

[54] PHOTOSENSITIVE POLYMERS AND PHOTORESIST COMPOSITIONS CONTAINING THE SAME

[75] Inventors: Sang-jun Choi, Kyungki-do; Chun-geun Park, Kyungki-do; Young-bum Koh, Seoul, all of Rep. of Korea

[73] Assignee: Samsung Electronics Co., Ltd., Kyungki-do, Rep. of Korea

[21] Appl. No.: 866,807

[22] Filed: May 30, 1997

[30] Foreign Application Priority Data

Aug. 5, 1996 [KR] Rep. of Korea ............... 1996-32631

[51] Int. Cl.⁶ .................................................. G03F 7/004
[52] U.S. Cl. ..................... 430/270.1; 430/910; 526/270; 526/282
[58] Field of Search ................... 430/270.1, 910; 522/31; 526/281, 270, 282

[56] References Cited

U.S. PATENT DOCUMENTS

| | | | |
|---|---|---|---|
| 4,591,626 | 5/1986 | Kawai et al. | 526/282 |
| 4,629,680 | 12/1986 | Iwasaki et al. | 430/910 |
| 4,681,833 | 7/1987 | Nagasawa et al. | 430/910 |
| 5,419,998 | 5/1995 | Mayes et al. | 403/905 |
| 5,443,690 | 8/1995 | Takechi et al. | 430/910 |
| 5,635,332 | 6/1997 | Nakano et al. | 430/270.1 |
| 5,665,518 | 9/1997 | Maeda et al. | 526/282 |

*Primary Examiner*—John S. Chu
*Attorney, Agent, or Firm*—Myers Bigel Sibley & Sajovec P.A.

[57] ABSTRACT

Photosensitive polymers are represented by the formula:

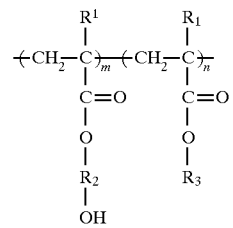

wherein R1 is selected from the group consisting of hydrogen and methyl; R2 is selected from the group consisting of aliphatic hydrocarbon groups having from 6 to 20 carbon atoms; R3 is selected from the group consisting of a t-butyl group and a tetrahydropyranyl group, and m and n are selected such that the ratio m/(n+m) ranges from 0.1 to 0.9. Photoresist compositions comprise the photosensitive polymers and photoacid generators.

24 Claims, 2 Drawing Sheets

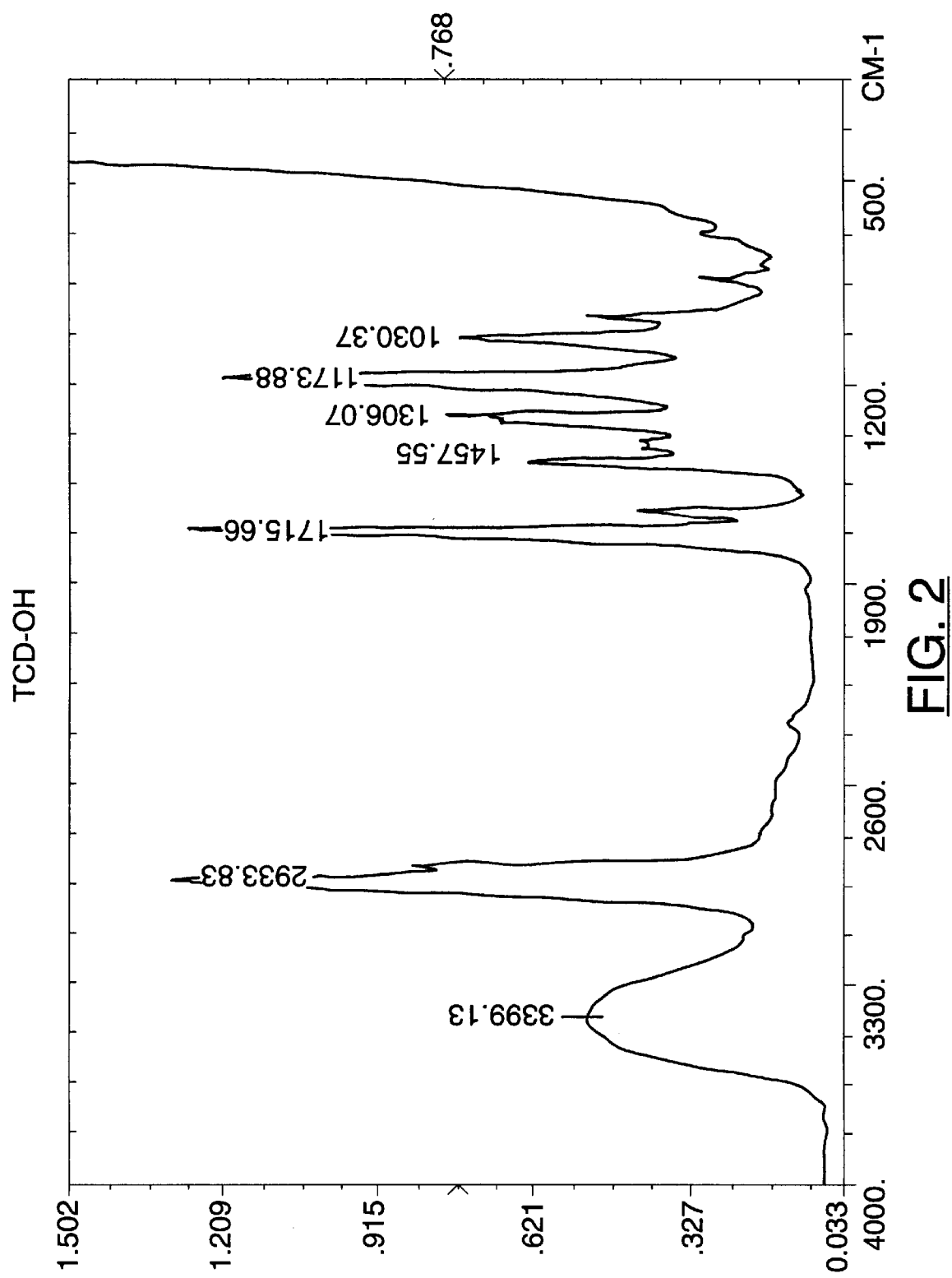

PHOTOSENSITIVE POLYMERS AND PHOTORESIST COMPOSITIONS CONTAINING THE SAME

FIELD OF THE INVENTION

The invention relates to photosensitive polymers and compositions thereof.

BACKGROUND OF THE INVENTION

With the increasing complexity of semiconductor manufacturing processes and integration of semiconductor devices, finer patterns of sub-quarter micron level are typically required in lithography processes. Accordingly, it would be desirable to develop new photoresist materials for use with an ArF eximer laser (193 nm) of shorter wavelengths as a light exposure source rather than using equipment which produce deep-ultraviolet (DUV) rays (248 nm).

The prerequisites for an adequately-performing photoresist are typically as follows: (1) high optical transparency at a wavelength of 193 nm; (2) strong etch resistance; and (3) excellent adhesiveness to attempt to suppress lifting of the photoresist film. Additionally, it would be desirable for the photoresist to be easily manufactured As an example, a methacrylate-based polymer has been developed as a potential new photosensitive polymer compound to be used for ArF. Although the methacrylate-based polymer arguably possesses good optical transparency at 193 nm, the polymer typically displays inadequate etch resistance. To address the problem associated with the methacrylate-based polymer, various functional groups have been proposed for incorporation onto this polymer. For example, such functional groups include alicyclic groups such as an adamantyl group, a norbornyl group, a tricyclodecanyl group, an isobornyl group, and the like.

An example of a conventional photosensitive compound is a polymer obtained by introducing one of the above-mentioned alicyclic groups to a tetrapolymer, for example iBMA-MMA-tBMA-MAA (isobornylmethacrylate-methylmethacrylate-t-butyl methacrylate-methacrylic acid). This polymer may be represented by the following formula:

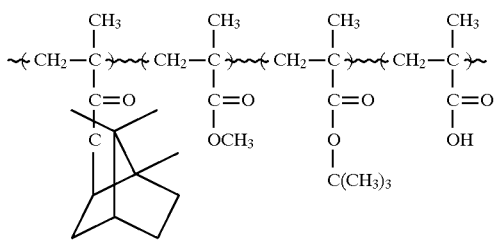

The above polymer is potentially disadvantageous. The polymer may be difficult to manufacture since four types of monomers are employed in polymerization. Moreover, etch resistance may not be significantly improved. Lifting of a photoresist film using the polymer may be experienced due to possible insufficient adhesiveness.

There is a need in the art for photosensitive polymers and photoresist compositions containing the same which address the problems set forth herein.

SUMMARY OF THE INVENTION

In view of the above, it is an object of the present invention to provide photosensitive polymers which display high optical transparency at shorter wavelenghts (e.g., 193 nm), strong etch resistance, and excellent adhesiveness.

It is another object of the present invention to provide photoresist compositions containing the photosensitive polymers.

These and other objects, features, and advantages of the present invention are provided by photosensitive polymers of the general formula:

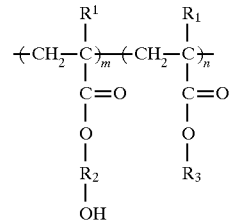

wherein $R_1$ is selected from the group consisting of hydrogen and methyl; $R_2$ is selected from the group consisting of aliphatic hydrocarbons having from 6 to 20 carbon atoms; $R_3$ is selected from the group consisting of a t-butyl group and a tetrahydropyranyl group, and m and n are selected such that the ratio $m/(n+m)$ ranges from 0.1 to 0.9.

The invention also relates to photoresist compositions. The photoresist compositions include photosensitive polymers of the general formula:

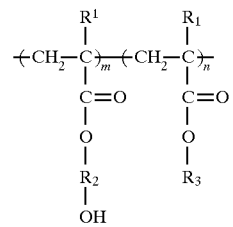

wherein $R_1$ is selected from the group consisting of hydrogen and methyl; $R_2$ is selected from the group consisting of aliphatic hydrocarbons having from 6 to 20 carbon atoms; $R_3$ is selected from the group consisting of a t-butyl group and a tetrahydropyranyl group, and m and n are selected such that the ratio $m/(n+m)$ ranges from 0.1 to 0.9; and photoacid generators.

BRIEF DESCRIPTION OF THE DRAWINGS

FIG. 2 is an IR spectrum of the monomer illustrated in FIG. 1.

DETAILED DESCRIPTION OF THE INVENTION

Figure 1:
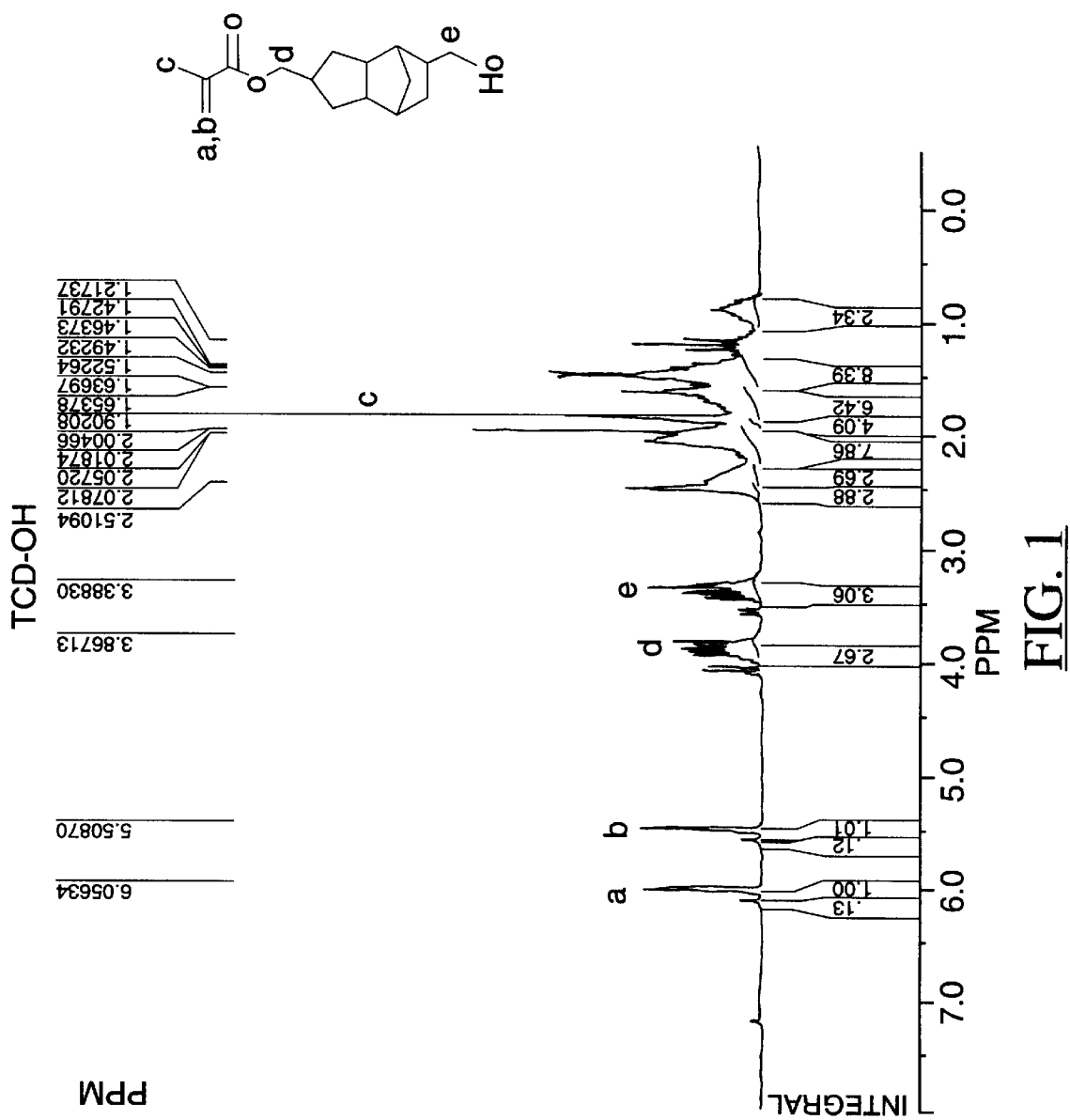
FIG. 1 is a nuclear magnetic resonance ($^1$NMR) of a monomer of a photosensitive polymer manufactured according to one embodiment of the present invention.

The present invention now will be described more fully hereinafter with reference to the accompanying specification and drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The invention relates to photosensitive polymers having the general formula:

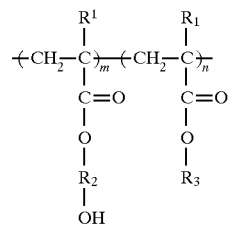

In the above formula, $R_1$ is selected from the group consisting of hydrogen and methyl; $R_2$ is selected from the group consisting of aliphatic hydrocarbons having from 6 to 20 carbon atoms; $R_3$ is selected from the group consisting of a t-butyl group and a tetrahydropyranyl group, and m and n are selected such that the ratio $m/(n+m)$ ranges from 0.1 to 0.9.

Various aliphatic hydrocarbon groups may be selected as $R_2$ in the formula above. As an example, $R_2$ may be a cyclic group. More preferably, $R_2$ may be selected from an alkyltricyclodecanyl group, an alkylnorbornyl group, and an alkyladamantyl group. In one embodiment, the alkyltricyclodecanyl group is a dimethylenetricyclodecanyl group. In a second embodiment, the alkylnorbornyl group is a norbornyl group. In a third embodiment, the alkyladamantyl group is a dimethyleneadamantyl group. In a fourth embodiment, $R_2$ is a decahydronaphthalene group.

The photosensitive polymers may have various molecular weights. Preferably, the photosensitive polymers have weight average molecular weights ranging from about 5,000 to about 200,000. More preferably, the weight average molecular weights range from about 10,000 to about 50,000.

The invention also relates to photoresist compositions. The photoresist compositions comprise photosensitive polymers of the formula:

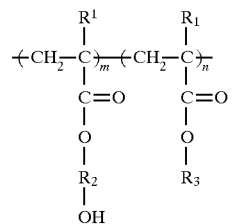

wherein $R_1$, $R_2$, $R_3$, n, and m are defined herein; and photoacid generators.

Various photoacid generators may be used in the photoresist compositions. Preferably, the photoacid generators are selected from the group consisting of triaryl sulfonium salt, diaryliodonium salt, and mixtures thereof. The photoacid generators may be used in various amounts in the photoresist compostions. Preferably, the photoresist compositions include from about 1 to about 20 weight percent of the photoacid generators based on the weight of the photosensitive polymers.

Although Applicants do not wish to be bound by any theories, it is believed that a photoreaction which occurs in a photoresist composition by exposure to light may be represented by the following reaction scheme:

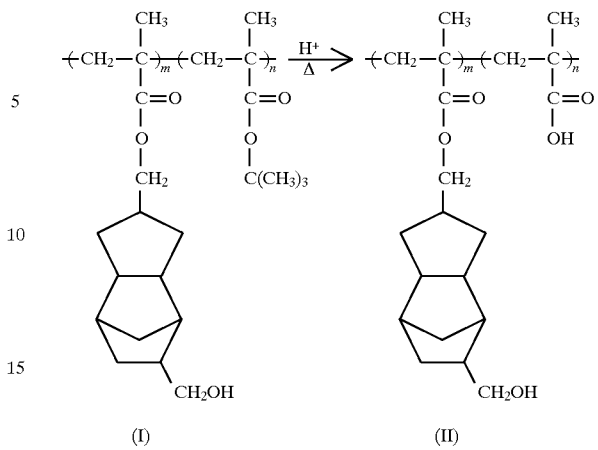

wherein m and n are defined herein.

As can be seen in the above reaction scheme, the polymer represented by the formula (I) has a t-butyl group at side chains which serve as dissolution-inhibiting groups. Thus prior to exposure, the photoresist composition formed from the photosensitive polymer does not appreciably dissolve in developing solution presumably due to the presence of the t-butyl group. During light exposure however, the t-butyl group is hydrolyzed by the acid (H+) catalytic reaction and is converted into a carboxyl group as illustrated in the polymer represented by the above formula (II). Accordingly, the polymer (II) readily disolves developing solution.

The photosensitive polymers and photoresist compositions of the invention are advantageous. The photosensitive polymers are generally more easily manufactured and less costly than conventional polymers since the photosensitive polymers are formed from only two monomers. Moreover, the etch resistance of the photoresist compositions are superior to conventional photoresist compositions formed of novolak resins. Also, lifting of photoresist films formed from the photoresist compositions typically does not occur primarily due to its excellent adhesiveness. Additionally, in contrast to conventional photoresist compositions, general developing liquids (e.g., 2.38 weight percent of tetramethyl ammonium hydroxide) may be used with the photoresist compositions of the invention.

The following examples are set forth for illustrating the invention, and are not to be interpreted as limiting thereof.

EXAMPLE 1

Synthesis of Tricyclodecanedimethanol Methacrylate

Tricyclodecanedimethanol methacrylate, which is a monomer for forming a photosensitive polymer, was synthesized via the following reaction scheme (1):

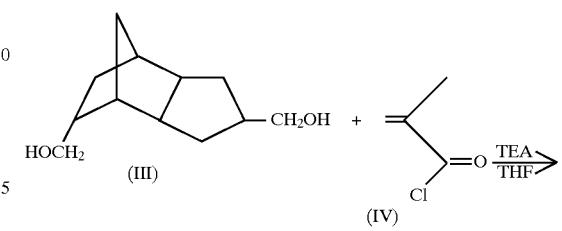

-continued
reaction scheme (1):

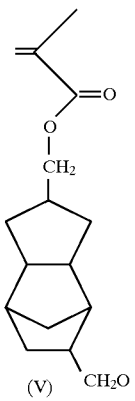

First, 30 g (0.15 mole) of tricyclo [5,2,1,0] decanedimethanol (III) and 16 g (0.15 mole) of triethylamine were dissolved in 300 ml of tetrahydrofuran. Then, 9.5 g (0.1 mole) of methacryloylchloride (IV) was slowly added thereto dropwise. Subsequently, the mixture reacted at 50° C. for about 12 hours. After the reaction was completed, the reaction product was poured into excess water and then extracted with diethyl ether (50 ml×4). The extracted product was dried in magnesium sulfate anhydride and then separated and purified by column chromatography (hexane:ethyl acetate=5:1) to obtain a reaction product (V) (yield: 60%). The reaction product (V) was subjected to $^1$NMR and IR spectral analyses (FIGS. 1 and 2, respectively) to be identified as tricyclodecanedimethanol methacrylate (TCD-OH). The spectral analyses are as follows:

H-$^1$NMR (CDCl$_3$) (ppm): 1.0~2.5 (m, 14H), 1.9 (s, 3H), 3.4 (m, 2H), 3.9 (m, 2H), 5.5 (s, 1 h), 6.0 (s, 1H)

IR (NaCl) (cm$^{-1}$): 3399 (=OH), 1715 (C=O), 1634 (C=C), 1174 (C—O)

EXAMPLE 2

Synthesis of 4-hydroxycyclohexyl methacrylate 4-hydroxycyclohexyl methacrylate, which is a monomer for forming a photosensitive polymer, was synthesized through the following reaction scheme (2):

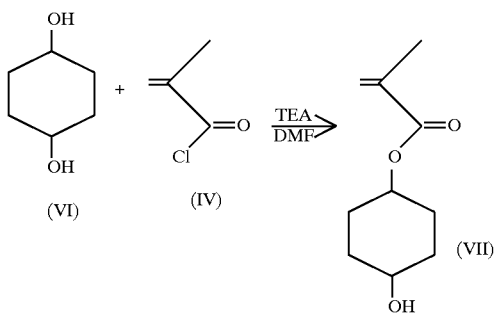

First, 18 g (0.15 mole) of 1,4-cyclohexanediol (VI) and 16 g (0.15 mole) of triethylamine were dissolved in 300 ml of dimethylformamide and then 9.5 g (0.1 mole) of methacryloylchloride (IV) was slowly added dropwise thereto. Subsequently, the resultant mixture was reacted at 60° C. for about 12 hours. After the reaction was completed, the reaction product was poured into excess water and then extracted with diethyl ether (50 ml×4). The extracted product was dried in magnesium sulfate anhydride and then separate and purified by column chromatography (hexane:ethyl acetate=5:1) to obtain reaction product (VII) (yield: 60%). The reaction product (VII) was subjected to $^1$NMR and IR spectral analyses to be identified as 4-hydroxycylohexyl methacrylate. The spectral analyses data are as follows:

H-$^1$NMR (CDCl$_3$) (ppm): 1.0~2.3 (m, 8H), 1.9 (s, 3H), 3.7 (m, 1H), 4.9 (m, 1H), 5.5 (s, 1H), 6.0 (s, 1H)

IR (NaCl) (cm$^{-1}$): 3397 (—OH), 1714 (C=O), 1634 (C=C), 1175

EXAMPLE 3

Synthesis of Copolymer of Tricyclodecanedimethanol Methacrylate and Methacrylate Derivative The reaction for manufacturing a copolymer by polymerizing the tricyclodecanedimethanol methacrylate (V) manufactured in Example 1 and methacrylate derivative (VIII) is expressed by the following reaction scheme (3):

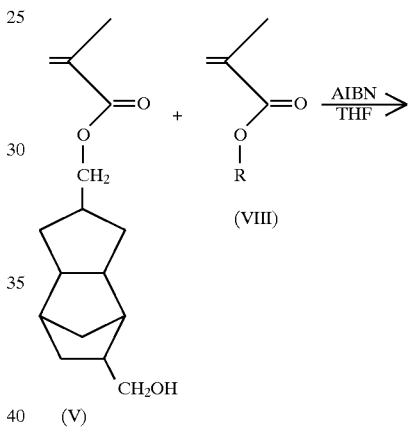

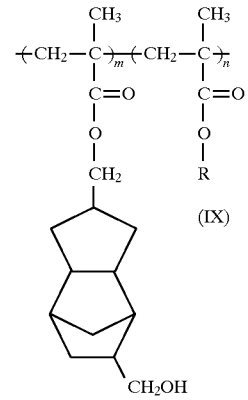

Synthesis of Copolymer when Methacrylate Derivative (VIII) is t-butylmethacrylate (R: t-butyl Group)

13 g (50 mmole) of tricyclodecanedimethanol methacrylate (V) and 6.6 g (50 mmole) of t-butylmethacrylate (VIII) were dissolved in 80 ml of tetrahydrofuran. 0.82 g of azobisisobutyronitrile (AIBN) was added thereto and purged with nitrogen (N$_2$) gas, thereby initiating the polymerization reaction of the above monomer compounds at 70° C. for 24 hours. After the polymerization was completed, the reaction product was poured into n-hexane to obtain a precipitation product. Subsequently, the precipitation product was dried in a vacuum oven at 50° C. for 24 hours to obtain reaction product (IX) (yield: 85%).

The reaction product (IX) had a weight-average molecular weight of 34,000 and a polydispersity (weight-average molecular weight/number-average molecular weight) of 2.3. Further, the reaction product (IX) was subjected to IR spectral analysis to be identified as a copolymer in which R is a t-butyl group. The IR spectral data were as follows:

IR (KBr) (cm$^{-1}$): 3461 (—OH), 2948, 1721 (C=O), 1378, 1149.

Synthesis of Copolymer when the Methacrylate Derivative (VIII) is Tetrahydropyranyl Methacrylate (R: Tetrahydropyranyl Group)

13 g (50 mmole) of tricyclodecanedimethanol methacrylate (V) and 8.5 g (50 mmole) of tetrahydropyranyl methacrylate (VIII) were dissolved in 85 ml of tetrahydrofuran. 0.82 g of azobisisobutyronitrile (AIBN) was added thereto and was purged with nitrogen (N$_2$) gas. The polymerization reaction of the above monomer compounds was carried out at 70° C. for 24 hours. After completing the polymerization, the reaction product was slowly dropped into excess water to obtain a precipitation product. Subsequently, the precipitation product was again dissolved in tetrahydrofuran and was reprecipitated in n-hexane to obtain a reaction product (IX) (yield: 83%).

The reaction product (IX) had a weight-average molecular weight of 31,000 and a polydispersity of 2.4. Further, the reaction product (IX) was subjected to IR spectral analysis to be identified as a copolymer in which R is a tetrahydropyranyl group. The IR spectral data were as follows:

IR (KBr) (cm$^{-1}$): 3460 (—OH), 2950, 1720 (C=O), 1455, 1150.

EXAMPLE 4

Synthesis of Copolymer of 4-hydroxycyclohexyl methacrylate and Methacrylate Derivative The reaction for manufacturing a copolymer by polymerizing the 4-hydroxycyclohexyl methacrylate (VII) manufactured in Example 2 and methacrylate derivative (VIII) is expressed by the following reaction scheme (4):

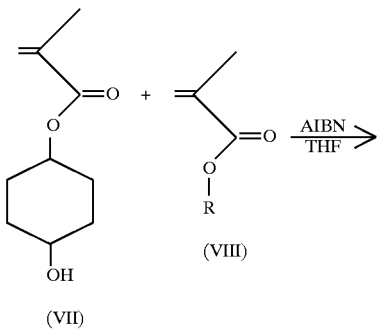

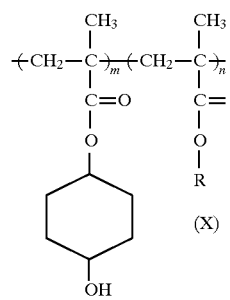

Synthesis of Copolymer when the Methacrylate Derivative (VIII) is t-butylmethacrylate (R: t-butyl Group)

9.1 g (50 mmole) of 4-hydroxycyclohexyl methacrylate (VII) and 6.6 g (50 mmole) of t-butylmethacrylate were dissolved in 70 ml of tetrahydrofuran. 0.82 g of azobisisobutyronitrile (AIBN) was added thereto and was purged with nitrogen (N$_2$) gas, thereby initiating the polymerization reaction of the above monomer compounds at 70° C. for 24 hours. After completing the polymerization, the reaction product was poured into n-hexane to obtain a precipitation product. Subsequently, the precipitation product was dried in a vacuum oven at 50° C. for 24 hours to obtain a reaction product (X) (yield: 85%).

The reaction product (X) has a weight-average molecular weight of 25,000 and a polydispersity of 2.2. Further, the reaction product (X) was subjected to IR spectral analysis to be identified as a copolymer in which R is a t-butyl group. The IR spectral data were as follows:

IR (KBr) (cm$^{-1}$): 3470 (—OH), 2952, 1718 (C=O), 1375, 1152.

Synthesis of Copolymer when the Methacrylate Derivative (VIII) is Tetrahydropyranyl Methacrylate (R: Tetrahydropyranyl Group)

9.1 g (50 mmole) of 4-hydroxycyclohexyl methacrylate (VII) and 8.5 g (50 mmole) of tetrahydropyranyl methacrylate were dissolved in 80 ml of tetrahydrofuran. 0.82 g of azobisisobutyronitrile (AIBN) was added thereto and was purged with nitrogen (N$_2$), thereby initiating the polymerization reaction of the above monomer compounds at 70° C. for 24 hours. After completing the polymerization, the reaction product was poured into excess water to obtain a precipitation product. Subsequently, the precipitation product was dissolved again in THF and was reprecipitated in n-hexane to obtain a reaction product (X) (yield: 85%).

The reaction product (X) had a weight-average molecular weight of 30,000 and a polydispersity of 2.4. Further, the reaction product (X) was subjected to IR spectral analysis and was identified as a copolymer in which R is a tetrahydropyranyl group. The IR spectral data were as follows:

IR (KBr) (cm$^{-1}$): 3462 (—OH), 2950, 1720 (C=O), 1456, 1152.

EXAMPLE 5

Formation of Photoresist Composition and Photoresist Film 1 g of the reaction product (IX) or (X) obtained in Example 3 or 4 was dissolved in 8 ml of propylene glycol monomethyl ether acetate (PGMEA). 0.02 g of triphenyl sulfonium triflate was added thereto and was stirred to form a photoresist composition.

The photoresist composition was coated on a silicone wafer surface-treated with hexamethyldisilizane to a thickness of 0.4 μm, baked at about 120° C. for 90 seconds (soft baking), exposed using a KrF eximer stepper having a numeric aperture of 0.45 and then the resultant product was developed for about 60 seconds using 2.38 wt % of tetramethyl ammonium hydroxide solution. Subsequently, the resultant product was baked again at about 130° C. for 90 seconds (hard baking) to form a photoresist film without lifting phenomenon.

Then, photolithography process was performed for the silicon wafer using the above-obtained photoresist film as a mask. As a result, an etch selection ratio of the photoresist film was found to be maintained within a proper range.

The photoresist of the present invention is transparent at 193 nm, is excellent in its resistance against an etching process, and displays good adhesiveness to remarkably reduce lifting phenomenon.

Many modifications and other embodiments of the invention will come to mind in one skilled in the art to which this invention pertains having the benefit of the teachings presented in the foregoing descriptions is and the associated drawings. Therefore, it is to be understood that the invention is not to be limited to the specific embodiments disclosed. Although specific terms are employed, they are used in a generic and descriptive sense only and not for purposes of limitation, and that modifications and embodiments are intended to be included within the scope of the appended claims.

That which is claimed:

1. A photosensitive polymer represented by the formula:

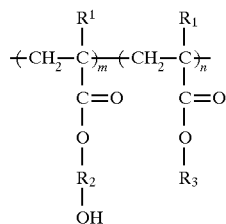

wherein $R_1$ is selected from the group consisting of hydrogen and methyl; $R_2$ is selected from the group consisting of aliphatic hydrocarbons having from 6 to 20 carbon atoms; $R_3$ is selected from the group consisting of a t-butyl group and a tetrahydropyranyl group, and m and n are selected such that the ratio m/(n+m) ranges from 0.1 to 0.9.

2. A photosensitive polymer according to claim 1, wherein $R_2$ is a cyclic group.

3. A photosensitive polymer according to claim 1, wherein $R_2$ is selected from the group consisting of an alkyltricyclodecanyl group, an alkylnorbornyl group, and an alkyladamantyl group.

4. A photosensitive polymer according to claim 2, wherein $R_2$ is selected from the group consisting of an alkyltricyclodecanyl group, an alkylnorbornyl group, and an alkyladamantyl group.

5. A photosensitive polymer according to claim 3, wherein the alkyltricyclodecanyl group is a dimethylenetricyclodecanyl group.

6. A photsensitive polymer according to claim 3, wherein the alkylnorbornyl group is a norbornyl group.

7. A photosensitive polymer according to claim 3, wherein the alkyladamantyl group is a dimethyleneadamantyl group.

8. A photosensitive polymer according to claim 1, wherein $R_2$ is a decahydronaphthalene group.

9. A photosensitive polymer according to claim 2, wherein $R_2$ is a decahydronaphthalene group.

10. A photosensitive polymer according to claim 1, wherein said photosensitive polymer has a weight average molecular weight ranging from about 5,000 to about 200,000.

11. A photosensitive polymer according to claim 10, wherein said photosensitive polymer has a weight average molecular weight ranging from about 10,000 to about 50,000.

12. A photoresist composition comprising:

a photosensitive polymer represented by the following formula:

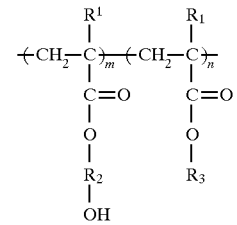

wherein $R_1$ is selected from the group consisting of hydrogen and methyl; $R_2$ is selected from the group consisting of aliphatic hydrocarbon groups having from 6 to 20 carbon atoms; $R_3$ is selected from the group consisting of a t-butyl group and a tetrahydropyranyl group, and m and n are selected such that the ratio m/(n+m) ranges from 0.1 to 0.9; and a photoacid generator.

13. A photoresist composition according to claim 12, wherein said photoresist composition comprises from about 1 to about 20 weight percent of said photoacid generator based on the weight of said photosensitive polymer.

14. A photoresist composition according to claim 12, wherein said photoacid generator is selected from the group consisting of triaryl sulfonium salt, diaryliodonium salt, and mixtures thereof.

15. A photoresist composition according to claim 12, wherein $R_2$ is a cyclic group.

16. A photoresist composition according to claim 12, wherein $R_2$ is selected from the group consisting of an alkyltricyclodecanyl group, an alkylnorbornyl group, and a alkyladamantyl group.

17. A photoresist composition according to claim 15, wherein $R_2$ is selected from the group consisting of an alkyltricyclodecanyl group, an alkylnorbornyl group, and an alkyladamantyl group.

18. A photoresist composition according to claim 16, wherein the alkyltricyclodecanyl group is a dimethylenetricyclodecanyl group.

19. A photoresist composition according to claim 16, wherein the alkylnorbornyl group is a norbornyl group.

20. A photoresist composition according to claim 16, wherein the alkyladamantyl group is a dimethyleneadamantyl group.

21. A photoresist composition according to claim 12, wherein $R_2$ is a decahydronaphthalene group.

22. A photoresist composition according to claim 15, wherein $R_2$ is a decahydronaphthalene group.

23. A photoresist composition according to claim 12, wherein said photosensitive polymer has a weight average molecular weight ranging from about 5,000 to about 200,000.

24. A photoresist composition according to claim 23, wherein said photosensitive polymer has a weight average molecular weight ranging from about 10,000 to about 50,000.

* * * * *